United States Patent [19]

Ermert et al.

[11] Patent Number: 4,796,183
[45] Date of Patent: Jan. 3, 1989

[54] ROTATING DATA TRANSMISSION DEVICE

[75] Inventors: Helmut Ermert, Röttenbach; Thomas Ulherr, Nürnberg; Albrecht Bär, Buckenhof, all of Fed. Rep. of Germany

[73] Assignee: Siemens Aktiengesellschaft, Berlin and Munich, Fed. Rep. of Germany

[21] Appl. No.: 914,236

[22] Filed: Oct. 2, 1986

[30] Foreign Application Priority Data

Oct. 25, 1985 [DE] Fed. Rep. of Germany ....... 3538035

[51] Int. Cl.⁴ .............................................. H05G 1/06
[52] U.S. Cl. .................................. 364/413.15; 378/4; 378/15
[58] Field of Search ...................... 364/414; 378/15, 4; 333/256; 343/763

[56] References Cited

U.S. PATENT DOCUMENTS

| | | | |
|---|---|---|---|
| 4,259,584 | 3/1981 | Krumme | 250/445 T |
| 4,323,781 | 4/1982 | Baumann et al. | 250/422 |
| 4,427,983 | 1/1984 | Kruger et al. | 343/763 |
| 4,533,887 | 8/1985 | Mörz et al. | 333/256 |
| 4,538,125 | 8/1985 | Beckmann et al. | 378/15 |
| 4,646,333 | 2/1987 | Yoshida et al. | 378/15 |

*Primary Examiner*—Jerry Smith
*Assistant Examiner*—Kim Thanh T. Bui
*Attorney, Agent, or Firm*—Hill, Van Santen, Steadman & Simpson

[57] ABSTRACT

A rotating data transmission device has a rotating part, such as a rotor, and a stationary part, such as a stator. One of the parts is in the form of a waveguide coupled to a set of transmitters. The other part has a set of receivers associated therewith, the number of transmitters being different from the number of receivers. The transmitters and receivers are respectively located at positions which guarantee continuous data transmission with no interruptions during relative movement of the parts. This results during transmission in certain waveguide sections which are not always required for primary data transmission, thus making those sections available for use as secondary transmission paths. The device is particularly suited for use in a computer tomograph apparatus for transmission of measured data and control data at a high rate.

6 Claims, 2 Drawing Sheets

ROTATING DATA TRANSMISSION DEVICE

BACKGROUND OF THE INVENTION

1. Field of the Invention

The present invention relates to a data transmission device for transmitting data between a rotating part and a stationary part, and in particular to such a device having a plurality of transmitters arranged on one part and a different plurality of receivers arranged on the other part.

2. Description of the Prior Art

A data transmission device is described in U.S. Pat. No. 4,259,584 having a rotor formed by the live ring of a computer tomograph on which an X-ray radiator and a radiation detector are disposed. Transmission of the data generated by the detector is undertaken with a ring of light-conducting material bent around the center of a pivot point, and a light source which emits light signals corresponding to the transmitted signals onto the surface of the ring of light conducting material. The ring conducts the incident light over its entire circumference, and has a coupling location at which a light receiver is arranged at the stationary part.

Other rotating data transmission devices for computer tomograph systems are disclosed in U.S. Pat. No. 4,323,781 and German AS 33 31 722. Another such device is disclosed in U.S. Pat. No. 4,427,983, wherein the data to be transmitted from a rotating annular part to a stationary annular part is achieved by discrete pluralities of transmitters and receivers. Still another rotating data transmission device having an annular waveguide and a single transmitter and a single receiver is disclosed in French Pat. No. 25 22 884.

SUMMARY OF THE INVENTION

It is an object of the present invention to provide a rotating data transmission device which has a simple structure and which permits data transmission without interruption at high data rates.

Another object of the present invention is to provide such a data transmission device, wherein a single data transmission path can form a plurality of transmission channels in which information can be transmitted in both directions.

The above objects are achieved in accordance with the principles of the present invention in a data transmission device wherein the data transmission path is symmetrically divided into a plurality of individual sub-paths, and wherein the transmitters and a different number of receivers are arranged so that the simultaneous transmission of data along a plurality of data links can be undertaken. Each data link is formed by a set of adjoining sub-paths, with the number of sub-paths in each link being fewer than the total number of sub-paths.

In an embodiment of the data transmission device disclosed herein which is particularly suited for use in a computer tomograph system for transmission at high data rates, the transmitters couple modulated radio-frequency waves into a waveguide, and the receivers decouple the waves which have been guided in the waveguide. A high data rate is thus achieved by the radio-frequency waves propagating within the waveguide.

DESCRIPTION OF THE PREFERRED EMBODIMENTS

Figure 1:
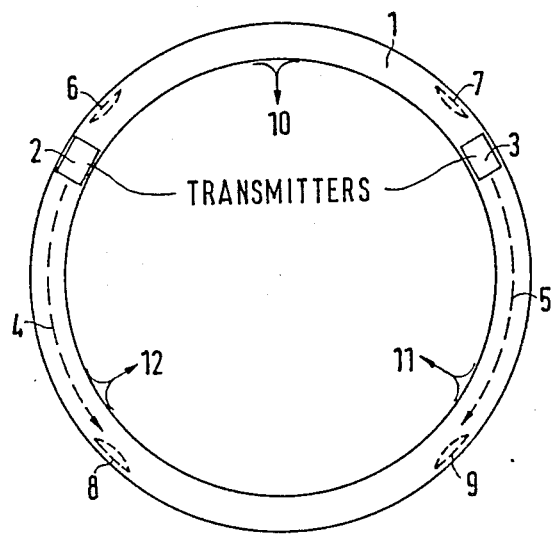
FIG. 1 is a side view showing the basic elements of a data transmission device constructed in accordance with the principles of the present invention.

A transmission device constructed in accordance with the principles of the present invention is shown in FIG. 1. The device includes a waveguide 1 to which two microwave transmitters 2 and 3 are attached. The microwave transmitters 2 and 3 transmit electromagnetic radiation into the waveguide 1 in the direction indicated by the arrows 4 and 5. Four symmetrically disposed wavesinks 6, 7, 8 and 9 divide the waveguide 1 into four sections of identical length. The waveguide 1, which constitutes a data transmission path, is thus divided into four sub-paths by the wavesinks 6, 7, 8 and 9. It is assumed in the embodiment shown in FIG. 1 that the waveguide 1 together with the transmitters 2 and 3 rotates, as indicated by the double arrow, and that data transmission proceeds from the two transmitters 2 and 3 to three stationary receivers 10, 11 and 12 schemmatically indicated in FIG. 1 and shown in greater detail in FIG. 2. The receivers 10, 11 and 12 are offset relative to each other by 120°. The two other waveguide sections of the four waveguide sections formed by the wavesinks can be used as a second data transmission link.

As a result of the selected different numbers of the transmitters and receivers, two transmitters and three receivers in the exemplary embodiment, continuous transmission of data is assured because one transmitter and one receiver always communicate with each other via a data link consisting of adjoining sub paths. The number of sub-paths in each link is fewer than the total number of sub-paths in the entire data transmission path formed by the waveguide 1. If the indicated position of the waveguide 1 in FIG. 1 corresponds to the zero degree position, the following allocation of receivers and transmitters occurs for rotation in a clockwire direction:

0°-60°: 3-11
60°-120°: 2-10
120°-180°: 3-12
180°-240°: 2-11
240°-300°: 3-10
300°-360°: 2-12

The use of a single waveguide for data transmission from a rotating to a stationary part results in a simple structure which is suitable for use in a computer tomograph system, as described in greater detail below. Direct coupling in of the data source to the transmission path occurs as shown by means of the two transmitters 2 and 3. Dead angles are avoided. When switching between the transmitters and receivers, phase discontinuities are also avoided, so that the device is suitable for transmission of data at a high rate.

Figure 2:
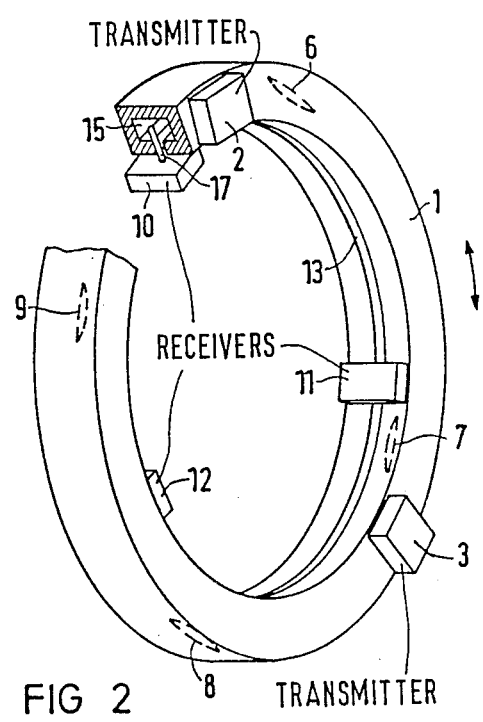
FIG. 2 is a more detailed perspective view, partly in section, of the data transmission device shown in FIG. 1.

Further details of the device are shown in FIG. 2. As can be seen in FIG. 2, the waveguide 1 is in the form of a ring having a rectangular cross-section with an interior slot 13. The two transmitters 2 and 3 are attached to a side face of the waveguide 1, and may be in the form of directed couplers emitting into the interior 15 of the waveguide 1 through the side face thereof.

Upon rotation of the waveguide 1, movement relative to the three stationary receivers 10, 11 and 12 occurs. Each of the receivers 10, 11 and 12 have a conductor or antenna, of which the conductor 17 of the receiver 10 can be seen in FIG. 2. The conductor 17, and the other conductors project through the slot 13 into the interior 15 of the waveguide 1 for picking up the microwave radiating propagating therein. The wavesinks, 6, 7, 8 and 9 are fashioned in a known manner by matched absorber structures disposed in the interior of the waveguide 1.

Figure 3:
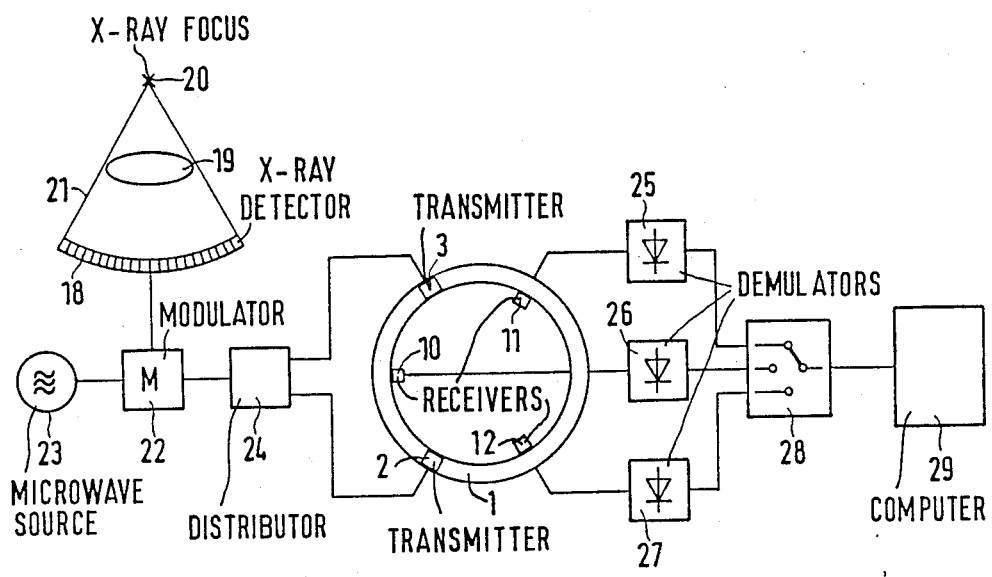
FIG. 3 is a block circuit diagram of the basic elements of a computer tomograph employing the data transmission device shown in FIGS. 1 and 2.

The use of a transmission device as shown in FIGS. 1 and 2 in a computer tomograph system is schematically illustrated in FIG. 3. The system includes an X-ray source, schematically indicated by the X-ray focus 20, which emits a fan-shaped X-ray beam 21 encompassing an examination subject 19. The radiation passing through the subject 19 is incident on a radiation detector 18 which may consist of a series of, for example, 512 detector elements. The data from the detector elements of the detector 18 are supplied to a modulator 22 which modulates the waves of a microwave source 23 in accordance with the data to be transmitted. The modulated microwaves are supplied to the two transmitters 2 and 3 via a distributor 24. The radiation picked up by the receivers 10, 11 and 12 is supplied through respective demodulators 25, 26 and 27 and a switch element 28 to a computer 29. The switch element 28 may, for example, be a multiplexer. From the transmitted data which are supplied during rotation of the detector and X-ray source with the waveguide 1 around the patient 19, the computer 29 calculates a cross-sectional image of the subject 19.

In the system shown in FIG. 3, the rotating portion of the system includes the waveguide 1, to which the X-ray source and the radiation detector 18 are rigidly connected. These elements are shown separately in FIG. 3 only for clarity.

It is also possible, however, to mount the waveguide 1 and the transmitters 2 and 3 in a stationary manner, and to rotate the receivers 10, 11 and 12 relative thereto with the X-ray source and there radiation detector.

Instead of two transmitters and three receivers, other suitable combinations can be selected. In accordance with the principles of the present invention, however, it is necessary that the respective numbers of transmitters and receivers differ by one, so that continuous data transmission occurs. With a subdivision of the waveguide into four sections of identical length by means of the four wavesinks, two channels are available for transmission in different directions if desired, or one channel is available for transmission in one direction. Given a larger number of separated waveguide sections, a larger number of data paths can be accomodated, however, this requires correspondingly increased switching circuitry amount the receivers.

Although modifications and changes may be suggested by those skilled in the art it is the intention of the inventors to embody within the patent warranted hereon all changes and modifications as reasonably and properly come within the scope of their contribution to the art.

We claim as our invention:

1. A data transmission device comprising:
   a stationary part and a rotating part;
   a first plurality of data transmitters mounted on either one said stationary part or said rotating part;
   a second plurality of data receivers mounted on the other of said stationary part or said rotating part, wherein said second plurality exceeds said first plurality by one;
   a circular data transmission path in the part in which said data transmitters are mounted, said path being in data transmitting communication with said data transmitters and said data receivers;
   wavesinks means for dividing said data transmission path into a plurality of symmetrical sub-paths of equal length; and
   means for arranging respective data transmitters and data receivers at selected locations around said data transmission path so that more than one of said transmitters can simultaneously transmit respective data via respective data links in said data transmission path as said rotating part rotates with respect to said stationary part, each data link constitutes a portion of total data transmission path and is formed by a number of adjoining sub-paths, with the number of said adjoining sub-paths in each data link being fewer than total number of sub-paths which are present in said circular data transmission path.

2. A data transmission device as claimed in claim 1, wherein said data transmission path is a waveguide, and wherein said data transmitters and data receivers are coupled to said waveguide for respectively emitting and receiving radiation therein.

3. A data transmission device as claimed in claim 2, wherein said waveguide is contained in said rotating part and wherein said data transmitters are attached thereto, and wherein said receivers are attached to said stationary part.

4. A data transmission device as claimed in claim 2, wherein said waveguide is contained in said stationary part, wherein said data transmitters are attached to said stationary part, and wherein said receivers are mounted on said rotating path.

5. A data transmission device as claimed in claim 1, wherein said first plurality is two and wherein said second plurality is three.

6. A data transmission device as claimed in claim 1, further comprising means connected to said rotating part for generating computer tomograph data, said means for generating computer tomograph data also being connected to said data transmitters, and further comprising means connected to said data receivers for analyzing said computer tomograph data and generating a cross-sectional image of an examination subject based thereon.

* * * * *